United States Patent [19]

Knuuttila et al.

[11] Patent Number: 5,183,796

[45] Date of Patent: Feb. 2, 1993

[54] CATALYST FOR METATHETIC REACTIONS OF HYDROCARBONS AND METHOD FOR FORMING THE CATALYST

[75] Inventors: Pekka Knuuttila, Porvoo; Eeva-Liisa Lakomaa, Espoo, both of Finland

[73] Assignee: Neste Oy, Espoo, Finland

[21] Appl. No.: 641,904

[22] Filed: Jan. 16, 1991

[30] Foreign Application Priority Data

Jan. 16, 1990 [FI] Finland ................................ 900254

[51] Int. Cl.$^5$ ........................ B01J 21/04; B01J 23/02; B01J 23/36

[52] U.S. Cl. .................................. 502/340; 502/300; 502/355

[58] Field of Search ........................ 502/300, 355, 340

[56] References Cited

U.S. PATENT DOCUMENTS 3,644,559  2/1972  Kobylinski et al. ............ 502/355 X
4,795,734  1/1989  Chauvin et al. ................. 502/300 X

FOREIGN PATENT DOCUMENTS 1105564  3/1968  United Kingdom .

OTHER PUBLICATIONS

Mouligjn, J. A. et al., J. Molec. Catal. 46, (1988), pp. 1 . . . 14.

Primary Examiner—W. J. Shine
Attorney, Agent, or Firm—Birch, Stewart, Kolasch & Birch

[57] ABSTRACT

The present invention concerns a heterogenic catalyst suited to the metathesis reactions of hydrocarbons in particular. Such a catalyst includes an inorganic oxide support, typically consisting of γ-alumina, having rhenium oxide absorbed onto its surface. The catalyst in accordance with the invention is prepared by vapourizing a precursor of rhenium, preferably rhenium heptoxide, preferably at a temperature of at least 160° C., and routing the vapour into a reaction chamber where they are brought to interaction with the support material. The temperature of the support material is kept above the condensation temperature of the vapour and simultaneously sufficiently high so as to attain the thermal activation energy level necessary for the generation of bonds between the rhenium oxide and the support material. According to the invention, the process is carried out preferredly within a temperature range of approx. 160° . . . 500° C. The rhenium oxide precursor is introduced in vapour phase in an amount, which is at least equal to or, preferably, in excess of the number of available binding sites on the support material surface. The activity of a catalyst even with a very low content of catalytic metal species is as high as the activity of a catalyst of appreciably higher content of rhenium that has been prepared by the methods of conventional technology.

20 Claims, No Drawings

CATALYST FOR METATHETIC REACTIONS OF HYDROCARBONS AND METHOD FOR FORMING THE CATALYST

BACKGROUND OF THE INVENTION

The present invention relates to a heterogenic rhenium containing catalyst suited particularly to the metathetic reactions of hydrocarbons.

Such a heterogenic catalyst generally contains an inorganic oxide support with a rhenium compound bound onto its surface. The terms metathesis, disproportionation or dismutation are used to indicate a catalytic reaction in which asymmetric olefinic molecules are converted into new olefins having a hydrocarbon chain longer or shorter than that of the precursor olefin. Thus, propene for instance reacts at the presence of said catalysts to yield ethene and butene. Further, two different kinds of olefinic molecules can react in a metathetic manner exemplified by the reaction of ethene and 2-butene yielding propene. Other areas of application of metathetic catalysts are, e.g., disproportionation by ring opening and the utilization of olefins having a carbon number of less than 10 and more than 20 that result from the oligomerization of ethene by way of isomerizing them first into i-olefins and then allowing them to react mutually at the presence of a metathetic catalyst. Another utilization method of said olefins is to allow them to react after isomerization with ethene at the presence of a metathetic catalyst to produce odd-carbon α-olefins, from which fractions suitable for raw materials of lubricants can be separated by way of fractionization.

DESCRIPTION OF RELATED ART

Catalysts for metathetic reactions are today prepared by conventional methods, which include the impregnation of a support with an active metal species from a solution of the metal salt, the co-precipitation of the metal salt and the support material and the coextrusion of the support and the precursor of the catalyst. Generally, the preparation of the catalyst also involves as an essential step the activation of the catalyst by heating at an elevated temperature at the presence of air or an inert gas. Typical catalysts of the above-described kind are the oxides of Re, W and Mo on a silica gel or an alumina support.

The above-described preparation methods of heterogenic catalysts are difficult to apply to the control of the adsorption of active catalyst materials onto the surface of the support material (that is, the dispersion of the catalyst).

The surface of powdered particles in support materials used in heterogenic catalysts is structurally inhomogeneous. Therefore, methods of conventional technology are poorly suited for controlled adsorption of a metal species or metal compound.

Moulijn, J. A. and Mol, J. C., J Molec Catal 46 (1988), p. 1 ... 14, propose that the number of active Re ions in metathetic reactions is less than 1% of the total Re content. Currently used catalysts contain, however, rhenium typically in the range >5 ... 20% w/w. Thus, it would be sufficient to adsorb only that amount of rhenium which is active in the reaction onto the support. No reference in the literature, however, is to be found disclosing results of metathetic activity for catalysts containing less than 1% w/w rhenium.

The GB patent publication 1,105,564 discloses a catalyst of disproportionation reactions for conversion of acyclic hydrocarbons, said catalyst containing the active compound adsorbed onto the support from vapour phase. According to the patent publication, the rhenium oxide containing catalyst is prepared by heating rhenium heptoxide in a carrier gas flow and allowing the rhenium heptoxide to sublime onto the surface of alumina support held at a low temperature. The heating temperature of the rhenium heptoxide is 150° ... 700° C. and the support surface temperature is 50° C. maximum. After the condensation, the catalyst is activated by heating to 500° ... 600° C. in air flow. Catalysts prepared by such a method according to the conventional technology have basically the same drawbacks as those described above.

DETAILED DESCRIPTION OF THE INVENTION

It is an object of the present invention to overcome the disadvantages associated with the conventional technology and to provide a novel type of catalyst, which contains rhenium on an inorganic oxide support.

The invention is based on the concept of evaporating a precursor of rhenium oxide, preferably rhenium heptoxide, preferably at a temperature of at least 160° C. and conducting the vapour into a reaction chamber, where it is brought into interaction with the support. The support temperature is maintained above the condensation temperature of the vapour and simultaneously so high as to attain the thermal activation energy necessary for generation of bonds between the rhenium (hept)oxide and the support material. According to the invention, the preferred operating temperature is about 160° ... 500° C. Preferably, the support material is amorphic γ-alumina. The rhenium heptoxide is introduced in the vapour phase in an amount at least equal to or, preferably, in an excess of the number of binding sites available on the support material surface.

More specifically, the catalyst in accordance with the invention is characterized in that the catalyst is prepared by vapourizing a precursor of rhenium oxide, routing the rhenium oxide precursor vapor into a reaction chamber where the vapour is reacted with the support material at about 160° to 500° C., maintaining the vapour pressure of the rhenium oxide precursor sufficiently high and the duration of the interaction with the support material sufficiently long so as to provide at least an equal amount of or, preferably, an excess of the rhenium oxide precursor in relation to the available binding sites of the support material, removing the rhenium oxide precursor not bound to the support material from the reaction chamber, and if necessary, posttreating the rhenium containing catalyst in order to modify its catalytic activity.

Interestingly, it has been discovered that by binding the catalytically active compound in the above-described manner onto the support, a heterogenic catalyst can be achieved whose activity at even very low contents of catalytic metal species is as high as the activity of such a catalyst of multiple content of catalytically active compound that has been prepared by way of prior art methods.

Lacking yet the full knowledge of all details related to the matter, we abstain from limiting our invention by any theoretical model. According to our opinion it is, however, possible that the structural geometry and electron distribution (potential energy function of the surface) determine the binding of the catalytically active rhenium compound to the different sites of the surface under the conditions in accordance with the invention. The rhenium compound is bound by chemisorption which takes place selectively at the surface sites.

According to the invention all reagents for pretreatment, for the binding or the metal species and for the optional posttreatment are brought into the reaction chamber in the vapour phase, typically one component at a time. Here, the vapour pressure of the evaporated catalytically active material or its compound is kept during the process sufficiently high and the duration of interaction with the support material surface sufficiently long so as to provide at least an equal amount of, preferably excess of the active material or its compound, respectively, at the binding sites of the support material. The proportion of excess active material used in relation to the concentration necessary to achieve full saturation of all available binding sites on the support material surface (customarily called a monolayer coverage) is typically 1.5- ... 1000-fold, preferably 2- ... 100-fold. The amount of the rhenium compound necessary for a monolayer coverage can be calculated from the area of the alumina support determined with the help of, e.g., the BET method, and from the known molecular structure of the support.

The reaction temperature must not fall below the temperature necessary for the evaporation of the reagent; otherwise, condensation or sublimation of the reagent could occur. Further, the reagent must not be allowed to condense on its way to the reaction space; therefore, the feed piping temperature must be kept at least at the vapourization temperature. The rhenium compound and the operating temperature must be selected so as to avoid decomposition of the metal compound or a possible condensation of its decomposition products.

Using experimental methods, it is possible to determine a temperature range, or temperature span, in which the reaction is most advantageously carried out. As explained above, the invention is applied at about 160° ... 500° C., preferably at about 175° ... 360° C. temperature. The lower limit of the given temperature range is determined by the condensation temperature of the rhenium heptoxide and by the activation energy necessary for establishing a desired surface bond. The upper limit is determined by the temperature at which the rhenium oxide chemisorbed on the support starts to show an essential rate of desorption from the desired binding states, that is, when the equilibrium of the chemisorption-desorption reaction has shifted toward desorption.

According to a preferred embodiment of the invention, a temperature gradient is arranged for the preparation of the catalyst rising from the source of the rhenium oxide precursor toward the reaction chamber. Thus, the rhenium heptoxide is evaporated at approx. 160° C. to 220° C., whereas the actual reaction is carried out at 175° to 360° C.

The reaction between the catalytically active material or its compound and the support can be carried out at ambient pressure, or alternatively, at overpressure. It is preferred, however, to carry out the reaction at reduced pressure. Typically, the operating pressure of the process is in the range from 0.1 to 100 mbar. Also, the possible pre- and post-treatment steps are preferably performed under reduced pressure. A benefit gained from the use of reduced pressure is that the reaction space is kept cleaner and the diffusion rate is increased. The reaction time is not particularly critical as long as it is sufficient to allow the evaporated reagent to interact with the binding sites of the support. Thence, the reaction time can be selected, for instance, in the range from 3 to 25 h.

The evaporated rhenium oxide precursor, typically rhenium heptoxide, can be brought to the reaction chamber as such, or alternatively, using an inert carrier gas such as nitrogen or noble gases. Advantageously, a protective gas atmosphere formed by an inert gas is used, whereby the same inert gas is used as the carrier gas for the rhenium oxide precursor vapour.

In the preparation of a catalyst according to the invention, the support can be subjected to a pretreatment at elevated temperatures prior to the actual binding reaction. The heat treatment can be applied to remove the physically adsorbed water and part of the chemisorbed water and hydroxyl groups from the support. The heat pretreatment is performed at, e.g., 200° ... 600° C. for 1 ... 40 h, advantageously for 2 ... 24 h. According to an alternative embodiment of the invention, the pretreatment is complemented with a chemical treatment, in which the support is modified by, e.g., a suitable metal compound such as magnesium dipivaloylmethane, or Mg(thd)2, or a similar easily volatile compound, prior to the actual reaction.

The catalyst can also be subjected to a posttreatment in order to modify its activity, particularly to activate the catalyst. Typically, the posttreatment is accomplished by heating at the presence of air, water vapour, hydrocarbon or inert gas. The applied temperature has been in the range 400° ... 1000 ° C.

During the preparation of the catalyst in accordance with the invention, different temperatures can be applied during pretreatment, binding of rhenium and posttreatment. A prerequisite for the procedures is, however, that all process steps are carried out above the condensation limit temperature $T_{min}$ for each reagent.

The invention achieves significant benefits. For instance, a low rhenium content in the catalyst results in a catalyst with an equal activity as a catalyst of appreciably higher rhenium content that has been prepared by the methods of the conventional technology. Further, the dispersion of the metallic material in the catalyst is more homogeneous than in catalysts prepared using liquid processes. The controllability of metal species binding during catalyst preparation is improved. Binding of several metal species becomes easier than from liquid phase. The metal species can be bound onto the support in the form of different compounds, whereby suitable ligands are provided in the catalyst.

The method in accordance with the invention has been applied to prepare catalysts for metathetic reactions that are based on rhenium compounds, in particular rhenium oxide, bound on onto a support material surface. A particularly favourable metal compound is $Re_2O_7$ (rhenium heptoxide) because of its assumed occurrence as an intermediate stage in all Re catalysts. In addition, the use of other evaporating Re compounds are applicable to the preparation of the catalysts.

Silica, alumina or their mixtures are advantageously used according to the invention as support materials capable of adsorbing a rhenium compound.

In the following, the invention will be illustrated with the help of exemplifying tests. It should be noted that the unit of activity g/g*h given in the activity tests indicates the quantity of reacted propene (in grams) per quantity of rhenium (g) and time (h).

EXAMPLES

Example 1

The catalysts were prepared using fine-grain alumina ($\gamma$-Al2O3) as support. The support material (4 g) was placed into the reaction chamber and heated at 400° C. at a nitrogen pressure of 3 mbar for 18 h. The purpose of the heat treatment was to remove the physically adsorbed water from the support and also a part of the chemically bonded water and OH groups. Next, the reaction space was cooled to 215° C. Rhenium heptoxide (99.99% $Re_2O_7$ by Aldrich Chemicals Co.) was heated to 175° C. and the evaporated rhenium heptoxide was routed in a nitrogen carrier stream into the reaction space for 225 minutes. The reaction space temperature during the entire binding process of Re was 215° C. Finally, the catalyst was cooled in nitrogen at 3 mbar pressure. The rhenium content of the catalyst was determined by instrumental neutron activation analysis (INAA). The rhenium content was 1.4% w/w.

The operation of the prepared catalyst was examined in the disproportionation reaction of propene to ethene and butene. The reaction is reversible ($\Delta H = 1.3$ kJ/mol) and the conversion of propene in the equilibrium is about 42%. Prior to the test, the catalyst was activated by heating in the reactor at 600° C. for 4 h in an dried air stream of 10 l/h. Then, the reactor was cooled to 150° C. and the propene feed was started at a rate of 1 l/min.

The results are given in Table 1A below.

TABLE 1A

| Time (h) | Ethene conversion (% w/w) | Butene conversion (% w/w) | Total conversion (% w/w) | Activity (g/g*h) |
|---|---|---|---|---|
| 0 | 9.8 | 27.7 | 45.8 | 95.9 |
| 2 | 3.5 | 11.4 | 16.8 | 35.2 |
| 4 | 2.4 | 8.1 | 11.2 | 23.4 |
| 5 | 2.1 | 6.9 | 9.7 | 20.3 |
| 7 | 1.6 | 5.4 | 7.7 | 16.1 |
|  | 1.3 | 4.5 | 6.5 | 13.6 |

Reference example 1

A reference catalyst was prepared by the conventional impregnation method as follows: An aqueous solution was prepared containing 1.45 g ammonium rhenate per 16 mol $H_2O$. The solution was transferred into a Schlenk flask containing the support (10.0 g). The contents were heated at approx. 80° C. under constant mixing in order to assure diffusion, the solvent was evaporated by vacuum and heating, and the catalyst was transferred into an oven and dried overnight at 120° C. Next, the catalyst was loaded into the reactor. The rhenium content of the catalyst was 7.5% w/w.

Using an identical procedure a catalyst with 0.5% w/w rhenium content was prepared. This catalyst was, however, inactive.

The activity of the prepared catalyst was examined in the disproportionation reaction of propene in a similar manner as in Example 1. The results are given in Table 1B below.

TABLE 1B

| Time (h) | Ethene conversion (% w/w) | Butene conversion (% w/w) | Total conversion (% w/w) | Activity (g/g*h) |
|---|---|---|---|---|
| 1.5 | 6.7 | 17.9 | 26.1 | 19.7 |
| 2.5 | 6.0 | 15.9 | 23.7 | 18.0 |
| 3.5 | 5.5 | 14.6 | 21.1 | 16.0 |
| 5.5 | 4.6 | 12.5 | 18.1 | 13.7 |
| 7.5 | 4.1 | 11.2 | 16.3 | 12.4 |
| 8.5 | 3.9 | 10.7 | 15.4 | 11.7 |
| 11.5 | 3.6 | 9.7 | 14.1 | 10.7 |

Example 2

UA rhenium catalyst was prepared identically with Example 1 with the exceptions that the preheating temperature of the support was 475° C., the pretreatment time was 18 h and the reactor temperature during the adsorption of the rhenium was 280° C. The rhenium content of the catalyst was 1.0% w/w.

The operation of the catalyst was tested in the disproportionation reaction of propene in a similar manner as in Example 1.

The results are given in Table 2 below.

TABLE 2

| Time (h) | Ethene conversion (% w/w) | Butene conversion (% w/w) | Total conversion (% w/w) | Activity (g/g*h) |
|---|---|---|---|---|
| 0 | 6.5 | 21.4 | 28.8 | 85.5 |
| 1 | 3.6 | 11.3 | 16.3 | 48.3 |
| 2 | 3.0 | 9.4 | 21.0 | 62.5 |
| 4 | 2.0 | 6.4 | 9.6 | 28.5 |
| 5 | 2.0 | 6.3 | 9.3 | 27.5 |
| 7 | 2.1 | 6.6 | 9.7 | 28.9 |
| 9 | 1.3 | 4.5 | 6.5 | 13.6 |

Example 3

A rhenium catalyst was prepared identically with Example 1 with the exceptions that the reactor temperature was 240° C. The rhenium content of the catalyst was 0.5% w/w.

The operation of the catalyst tested in the disproportionation reaction of propene in a similar manner as in Example 1.

The results are given in Table 3 below.

TABLE 3

| Time (h) | Ethene conversion (% w/w) | Butene conversion (% w/w) | Total conversion (% w/w) | Activity (g/g*h) |
|---|---|---|---|---|
| 0 | 0.0 | 0.0 | 100 | 653.6 |
| 1 | 1.7 | 5.5 | 8.0 | 52.5 |
| 2 | 1.2 | 4.0 | 12.5 | 81.8 |
| 4 | 1.0 | 3.1 | 4.9 | 32.4 |
| 5 | 0.8 | 2.5 | 4.2 | 27.4 |
| 7 | 0.8 | 2.3 | 3.9 | 25.5 |
| 9 | 0.6 | 2.0 | 3.5 | 22.6 |

Example 4

A rhenium catalyst was prepared identically with Example 1 with the exceptions that the preheating step simply comprised the heating of the support to 360° C. at 3 mbar nitrogen pressure, with a direct continuation of the reaction at the same temperature. The rhenium content of the catalyst was 0.04% w/w.

The operation of the catalyst was tested in the disproportionation reaction of propene in a similar manner as in Example 1.

The results are given in Table 4 below.

TABLE 4

| Time (h) | Ethene conversion (% w/w) | Butene conversion (% w/w) | Total conversion (% w/w) | Activity (g/g*h) |
|---|---|---|---|---|
| 0.5 | 0.3 | 1.0 | 1.7 | 73.8 |
| 1 | 0.3 | 0.9 | 1.5 | 66.2 |
| 2 | 0.6 | 1.0 | 2.1 | 94.1 |
| 4 | 0.4 | 0.9 | 1.7 | 75.5 |
| 5 | 0.4 | 0.7 | 1.4 | 62.8 |
| 7 | 0.4 | 0.0 | 0.6 | 24.5 |

Example 5

In addition to this, tests were performed to investigate how an addition of Mg(thd)2 affects the capacity of the support for rhenium binding. The Mg(thd)2 was prepared as described in a paper by Hammon, G. S. et al., Inorg Chem 2 (1963), p. 73. The alumina support was first treated at 475° C. for 18 h, then cooled to 240° C., after which the Mg(thd)2 was evaporated at 75°... 85° C. and the vapour was brought into contact with the support. Of the rhenium heptoxide used, 0.36% was bound as rhenium onto the support. In a reference test, in which magnesium dipivaloylmethane was not used, the content of bound rhenium remained at 0.12%. Thus, the Mg(thd)2 treatment tripled the content of bound rhenium.

What is claimed is:

1. A heterogenic catalyst particularly suited for liquid- or vapour-phase metathetic reactions of hydrocarbons, said catalyst containing rhenium oxide bound onto an inorganic support material, wherein said catalyst is prepared by a method comprising the steps of:
   vapourizing rhenium heptoxide precursor,
   routing the rhenium heptoxide precursor vapour into a reaction chamber where the vapour is reacted with the support material at a temperature of about 160° to 500° C.,
   maintaining the vapour pressure of the rhenium heptoxide precursor sufficiently high and the duration of the interaction with the support material sufficiently long so as to provide at least an equal amount of or an excess of the rhenium heptoxide precursor in relation to the available binding sites of the support material, and
   removing the rhenium heptoxide precursor not bound to the support material from the reaction chamber to form said heterogenic rhenium oxide containing catalyst.

2. The catalyst in accordance with claim 1, wherein the rhenium heptoxide is vapourized at a temperature of approximately 160° C. to 220° C. and the rhenium heptoxide vapour is reacted with the support material at a temperature of approximately 175° to 360° C.

3. The catalyst in accordance with claim 1, wherein the rhenium heptoxide precursor is reacted with the support material at a pressure of 0.1 to 100 mbar.

4. The catalyst in accordance with claim 1, wherein the support material is first heated for 1 to 40 hours at a temperature of 200° to 600° C., before the rhenium oxide vapour is reacted with the support material.

5. The catalyst in accordance with claim 4, wherein after the preheating stage, the support material is treated with magnesium dipivaloylmethane.

6. The catalyst in accordance with claim 1, wherein the reaction time between the rhenium heptoxide precursor and the support material is 3 to 25 hours.

7. The catalyst in accordance with claim 9, wherein the posttreatment is performed by heating in the presence of air, water vapour, hydrocarbon or an inert gas.

8. The catalyst in accordance with claim 1, wherein the support material is gamma-alumina.

9. The catalyst in accordance with claim 1, wherein after the rhenium heptoxide precursor is removed from the reaction chamber, the rhenium oxide containing catalyst is posttreated to modify its catalytic activity.

10. A method for forming a heterogenic catalyst particularly suited for liquid- or vapour-phase metathetic reactions of hydrocarbons, said catalyst containing a rhenium oxide bound onto an inorganic support material, wherein said method comprises the steps of:
   vapourizing a rhenium heptoxide precursor,
   routing the rhenium heptoxide precursor vapour into a reaction chamber where the vapour is reacted with the support material at a temperature of about 160° to 500° C.,
   maintaining the vapour pressure of the rhenium heptoxide precursor sufficiently high and the duration of the interaction with the support material sufficiently long so as to provide at least an equal amount of or an excess of the rhenium heptoxide precursor in relation to the available binding sites of the support material, and
   removing the rhenium heptoxide precursor not bound to the support material from the reaction chamber to form said heterogenic rhenium oxide containing catalyst.

11. The method of claim 10, wherein after the rhenium heptoxide precursor is removed from the reaction chamber, it is posttreated to modify its catalytic activity.

12. The method of claim 10, wherein the rhenium heptoxide is vapourized at a temperature of approximately 160° to 220° C. and the rhenium heptoxide vapour is reacted with the support material at a temperature of approximately 175° to 360° C.

13. The method of claim 10, wherein the rhenium heptoxide precursor is reacted with the support material at a pressure of 0.1 to 100 mbar.

14. The method of claim 10, wherein the support material is first heated for 1 to 40 hours at a temperature of 200° to 600° C., before the rhenium heptoxide vapour is reacted with the support material.

15. The method of claim 10, wherein the preheating stage, the support material is treated with magnesium dipivaloylmethane.

16. The method of claim 10, wherein the reaction time between the rhenium heptoxide precursor and the support material is 3 to 25 hours.

17. The method of claim 11, wherein the posttreatment is performed by heating in the presence of air, water vapour, hydrocarbon or an inert gas.

18. The method of claim 10, wherein the support material is gamma-alumina.

19. A method for forming a heterogenic catalyst particularly suited for liquid- or vapour-phase metathetic reactions of hydrocarbons, said catalyst containing a rhenium oxide bound onto tan inorganic support material, wherein said method comprises the steps of:
   vapourizing a rhenium heptoxide precursor at a temperature of approximately 160° to 220° C.;
   routing the rhenium heptoxide precursor vapour into a reaction chamber where the vapour is reacted with the support material at a temperature of approximately 175° to 360° C. and a pressure of 1 to 100 mbar, wherein the support material is first heated for 1 to 40 hours at a temperature of 200° to 600° C. before being reacted with the rhenium oxide precursor;

maintaining the vapour pressure of the rhenium heptoxide precursor sufficiently high and the duration of the interacting with the support material for 3 to 25 hours so as to provide at least an equal amount of or an excess of the rhenium heptoxide precursor in relation to the available binding sites of the support material, and removing the rhenium heptoxide precursor not bound to the support material from the reaction chamber to form said heterogenic rhenium oxide containing catalyst.

20. The method of claim 10, wherein the support material is gamma-alumina.

* * * * *